(12) United States Patent
Gan

(10) Patent No.: US 6,924,120 B1
(45) Date of Patent: Aug. 2, 2005

(54) CHAPERONE PROTEIN CONTAINING AN INTRAMOLECULAR CHAPERONE-LIKE SEQUENCE AND ITS APPLICATION TO INSULIN PRODUCTION

(75) Inventor: Zhong-Ru Gan, Tonghua (CN)

(73) Assignee: Tonghua Gantech Biotechnology, Ltd., Tonghua (CN)

( * ) Notice: Subject to any disclaimer, the term of this patent is extended or adjusted under 35 U.S.C. 154(b) by 0 days.

(21) Appl. No.: 09/423,100

(22) PCT Filed: Mar. 31, 1998

(86) PCT No.: PCT/CN98/00052

§ 371 (c)(1),
(2), (4) Date: Dec. 11, 2000

(87) PCT Pub. No.: WO99/50302

PCT Pub. Date: Oct. 7, 1999

(51) Int. Cl.[7] ............................ C12P 21/06; C12N 9/00; C07K 5/00; C07K 14/62; C07K 14/61
(52) U.S. Cl. ...................... 435/68.1; 435/183; 530/300; 530/399
(58) Field of Search ............................ 435/68.1, 183, 435/69.4, 226, 320.1, 325; 530/300, 399, 350, 303; 536/23.2

(56) References Cited

U.S. PATENT DOCUMENTS

| | | | |
|---|---|---|---|
| 4,342,832 A | | 8/1982 | Goeddel et al. |
| 4,665,160 A | * | 5/1987 | Seeburg ...................... 530/399 |
| 4,916,212 A | * | 4/1990 | Markussen et al. ......... 530/303 |
| 5,254,463 A | | 10/1993 | de Boer et al. |
| 5,358,857 A | | 10/1994 | Stengelin et al. |
| 5,422,110 A | | 6/1995 | Potter et al. |
| 5,473,049 A | | 12/1995 | Obermeier et al. |
| 5,559,128 A | | 9/1996 | Chakravarty et al. |
| 5,719,021 A | | 2/1998 | Inouye |
| 6,001,604 A | | 12/1999 | Hartman et al. |
| 2002/0164712 A1 | * | 11/2002 | Gan .......................... 435/69.4 |

FOREIGN PATENT DOCUMENTS

| | | |
|---|---|---|
| CA | 1341211 | 3/2001 |
| EP | 0 055 945 | 7/1982 |
| EP | 0 645 454 A2 | 3/1995 |
| WO | WO 96/20724 | 7/1996 |
| WO | 98/23888 A1 | 8/1996 |
| WO | WO 97/18233 | 5/1997 |
| WO | WO 02/079251 A2 * | 10/2002 ........... C07K/14/62 |

OTHER PUBLICATIONS

Moore & Kelly (May 22, 1986) "Re-routing of a secretary protein by fusion with human growth hormone sequences." Nature 321(6068): 443–446.*

Cattini & Eberhardt (Feb. 11, 1987) "Regulated expression of chimaeric genes containing the 5'-flanking regions of human growth hormone-related genes in transiently transfected rat anterior pituitary tumor cells." Nucleic Acids Research 15(3): 1297–.*

Gell et al. (Aug. 1, 1989) "Synthesis and sequence-specific proteolysis of a hybrid protein (colicin A::growth hormone releasing factor)produced in *Escherichia coli*." Gene 80(1): 129–136.*

Hirt et al. (Feb. 1987) "The Human Growth Hormone Gene Locus: Structure, Evolution, and Allelic Variations." DNA 6(1): 59–70.*

Liebhaber et al. (Oct. 25, 1986) "Synthesis of Growth Hormone-Prolactin Chimeric Protein and Processing Mutants by the Exchange and Deletion of Genomic Exons." The Journal of Biological Chemistry 261(30): 14301–14306.*

Bork et al . 1996, Trends in Genetics 12:425–427.*

Brenner, 1999, Trends in Genetics 15:132–133.*

Smith et al., 1997, Nature Biotechnology 15:1222–1223.*

Doerks et al., 1998, Trends in Genetics 14:248–250.*

Skolnick et al., 2000, Trends in Biotech. 18(1): 34–39.*

Bork, 2000, Genome Reserch 10:398–400.*

Ngo et al., 1994. The Protein Folding Problem and Tertiary Structure Prediction, pp. 492–295.*

Wells, 1990, Biochemistry 29: 8509–8517.*

Samuelsson et al., 1994, "Enhanced in vitro refolding of insulin-like growth factor J using a solubilizing fusion partner," Biochemistry 33(14):4207–4211 (abstract).

Klappa et al., 1997, "Interactions between protein disulphide isomerase and peptides." *European Journal of Biochemistry* 248(1):37–42 (abstract).

U. Shinde and M. Inouye, "Intramolecular chaperones and protein folding," *TIBS*, (1993), vol. 18, pp. 442–446.

M. Inouye, "Intramolecular Chaperone: The Role of the Pro–Peptide in Protein Folding," *Enzyme*, (1991), vol. 45, pp. 314–321.

(Continued)

*Primary Examiner*—Brenda Brumback
*Assistant Examiner*—Christopher James Nichols
(74) *Attorney, Agent, or Firm*—Townsend and Townsend and Crew LLP

(57) ABSTRACT

The present invention relates to a chimeric protein containing an intramolecular chaperone (IMC) like sequence linked to a target protein, preferably an insulin precursor. The present invention also relates to a process for obtaining a correctly folded insulin-precursor-contain chimeric protein, comprising, inter alia, contacting an incorrectly folded chimeric protein containing an IMC like sequence linked to an insulin precursor with at least one chaotropic auxiliary agent. The present invention further relates to an assay for screening an amino acid sequence for the ability to improve folding of an insulin precursor using a chimeric protein containing an IMC like sequence linked to an insulin precursor.

37 Claims, 2 Drawing Sheets

OTHER PUBLICATIONS

Figure 1A:
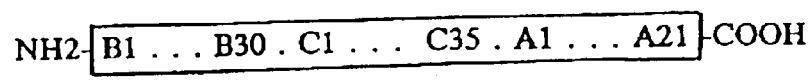

M. Ikehara, et al., "Synthesis of a gene for human growth hormone and its expression in *Escherichia coli*," *Proc. Natl. Acad. Sci USA*, (Oct. 1984), vol. 81, pp. 5956–5960.

Watson et al., Recombinant DNA—A Short Course, Scientific American Books, W.H. Freeman Co., NY, (1983), pp. 231–241.

Norman and Litwack, "Pancreatic Hormones: Insulin and Glucagon," in Hormones, Academic Press, Inc., NY, (1987), pp 264–317.

I. Johnson, "Human Insulin from Recombinant DNA Technology," *Science*, (Feb. 11, 1983), vol. 219, pp. 632–637.

D. Williams, et al., "Cytoplasmic Inclusion Bodies in *Escherichia coli* Producing Biosynthetic Human Insulin Proteins," *Science,* (Feb. 5, 1982), vol. 215, pp. 687–689.

R. Burgess, "Protein Purification," in *Protein Engineering,* Oxender, D.L., Fox, C.F., Eds.; Alan R. Liss, Inc. NY, (1987), pp. 71–82.

R.E. Chance, et al., "The Production of Human Insulin Using Recombinant DNA Technology and a New Chain Combination Procedure," in *Peptides: Synthesis–Structure–Function,* Pierce Chem. Co., Rockford, Il, (1981), pp. 721–728.

B.H. Frank and R.E. Chance, "The Preparation and characterization of human insulin of recombinant DNA origin," in Therapeutic Agents Produced by Genetic Engineering "Quo Vadis?" Symposium. (May 29–30, 1985), Sanoff Group, Toulouse–Labège, France, pp 137–148.

R E Chance, et al., "Chemical, Physical, and Biological Properties of Recombinant Human Insulin." in J. L. Gueriguian *Insulins, Growth Hormone, and Recombinant DNA Technology*, Raven Press, NY, (1981), pp. 71–85.

R. D. Johnson, "The Processing of Biomacromolecules: A Challenge for the Eighties," *Fluid Phase Equilib.,* (1986), 29:109–123.

D. V. Goeddel, et al., "Expression in *Escherichia coli* of chemically synthesized genes for human insulin," *Proc. Natl. Acad. Sci. USA*. (Jan. 1979), No. 1, pp. 106–110.

J. P. Burnett, "Commercial Production of Recombinant DNA–Derived Products," in *Experimental Manipulation of Gene Expression*, Academic Press, NY, (1983), pp. 259–277.

J. Etienne–Decent, "Regulation of Protein Synthesis," in *Genetic Biochemistry: From Gene to Protein,* Ellis Horwood Limited, Chichester, U.K., (1988), pp. 125–127.

S. M. Wheelwright, *Protein Purification: Design and Scale up of Downstream Processing*, Oxford University Press; NY, (1991), p. 217.

B.H. Frank and R.E. Chance, "Two Routes for Producing Human Insulin Utilizing Recombinant DNA Technology," *Munch. Med. Wschr.,* (1983), vol. 125, Suppl. 1, pp. S14–S20.

E. P. Kroeff, et al, "Production Scale Purification of Biosynthetic Human Insulin by Reversed–Phase High–Performance Liquid Chromatography," *Journal of Chromalography*, (1989), vol. 461, pp. 45–61.

H. V. Tottrup and S. Carlsen, "A Process for the Production of Human Proinsulin in *Saccharomyces cerevisiae."* *Biotechnol. Bioeng.,* (1990), vol. 35, pp. 339–348.

L. R. Castellanos–Serra, et al., "Expression and folding of an interleukin–2–proinsulin fusion protein and its conversion into insulin by a single step enzymatic removal to the C–peptide and the N–terminal fused sequence," *FEBS Letters,* (1996), vol. 378, pp. 171–176.

L. Villa–Komaroff, et al., "A bacterial clone synthesizing proinsulin," *Proc. Natl. Acad. Sci. USA,* (Aug. 1978), vol. 75, No. 8, pp. 3727–3731.

L. Thim, et al., "Secretion and processing of insulin precursors in yeast." *Proc. Natl. Acad. Sci. USA*. (Sep. 1986), vol. 83, pp. 6766–6770.

I V Diers et al., "Yeast Fermentation Processes for Insulin Production," in Y. H. Chiu *Drug Biotechnology Regulations: Scientific Basis and Practices,* Marcel Dekker. Inc., NY, (1991), pp. 166–176.

M. R. Ladisch and K. L. Kohlmann, "Recombinant Human Insulin," *Biotechnol. Prog.,* (1992), vol. 8, pp. 469–478.

* cited by examiner

CHAPERONE PROTEIN CONTAINING AN INTRAMOLECULAR CHAPERONE-LIKE SEQUENCE AND ITS APPLICATION TO INSULIN PRODUCTION

1. BACKGROUND OF THE INVENTION

1.1. Technical Field

The present invention relates to a chimeric protein containing an intramolecular chaperone (IMC) like sequence linked to a target protein. In particular, the invention relates to a chimeric protein containing an IMC like sequence linked to an insulin precursor. The present invention also relates to a process for obtaining a correctly folded insulin-precursor-containing chimeric protein, comprising, inter alia, contacting an incorrectly folded chimeric protein containing an IMC like sequence linked to an insulin precursor with at least one chaotropic auxiliary agent. The present invention further relates to an assay for screening an amino acid sequence for the ability to improve folding of an insulin precursor using a chimeric protein containing an IMC like sequence linked to an insulin precursor.

1.2. Background Art

1.2.1. Intramolecular Chaperones and Protein Folding

Molecular chaperones are defined as a class of proteins that assist correct folding of other polypeptides but are not components of the functional assembled structure (Shinde and Inouye, *TIBS*, 1993, 18:442–446). Intramolecular chaperones (IMCs) are part of the precursors of the target proteins to be folded and in their absence the target protein molecules do not have enough information for proper self-folding (Inouye, *Enzyme*, 1991 45:314–321). Unique features of IMCs include: a) the IMC and the target protein are linked by a peptidyl bond forming a single polypeptide; b) the IMC is absolutely required for the formation of active conformation of the target protein, but not required for the function of the target protein; c) upon completion of the protein folding, the IMC is removed either by autoprocessing or by another endopeptidase; d) the IMC does not function as a catalyst, i.e., one IMC molecule is able to refold only one molecule of the target protein; and e) the IMC is a highly specific "tailor-made" polypeptide which works only for the target proteins (Inouye, *Enzyme*, 1991, 45:314–321).

Recently, it has been shown that an IMC or propeptide can help the target protein fold intermolecularly, i.e., the IMC or propeptide is not linked to the target protein via a peptidyl bond, but rather is added to the folding reaction as a separate peptide (U.S. Pat. No. 5,719,021). However, it is noteworthy that the propeptide used in the U.S. Pat. No. 5,719,021 is the natural propeptide of the target protein or a propeptide of a polypeptide that has the same function of the target protein and the polypeptide also has an amino acid sequence that is similar to the target protein. In addition, the intermolecular reaction described in the U.S. Pat. No. 5,719,021 must be carried out in a buffered ionic aqueous medium favoring hydrophobic interaction.

Examples of IMCs include the propeptides of subtilisin, α-lytic protease, carboxypeptidase Y and ubiquitin (Shinde and Inouye, *TIBS*, 1993, 18:442446). Certain characteristics of an IMC sequence of subtilisin include: a) the IMC contains a higher percentage of charged amino acid residues than the target protein; b) the distribution of these charged residues within the IMC is extremely uneven, i.e., the N-terminal half contains more positively charged residues than negatively charged residues and the C-terminal half contains more negatively charged residues than positively charged residues; c) Ser and Thr residues within the IMC are also unevenly distributed; d) the IMC contains a reactively high content of aromatic residues, and e) the IMC contains a hydrophobic sequence of 9 residues (Inouye, *Enzyme*, 1991, 45:314–321). A similar bias towards charged residues is also observed in α-lytic protease and carboxypeptidase Y (Inouye, *Enzyme*, 1991, 45:314–321).

1.2.2. Amino Acid Sequence of Mature Human Growth Hormone

The amino acid sequence of mature human growth hormone (hGH) is disclosed in Ikehara et al., *Proc. Natl. Acad. Sci. USA*, 1984, 81:5956–5960. There is no suggestion in the art that mature hGH or any portion thereof can function as an IMC or propeptide. Actually, mature hGH or any portion thereof can not be considered a propeptide at all because by definition, any pre, pro, or prepro sequence is removed from a mature sequence.

1.2.3. Human Insulin Structure

Figure 1B:
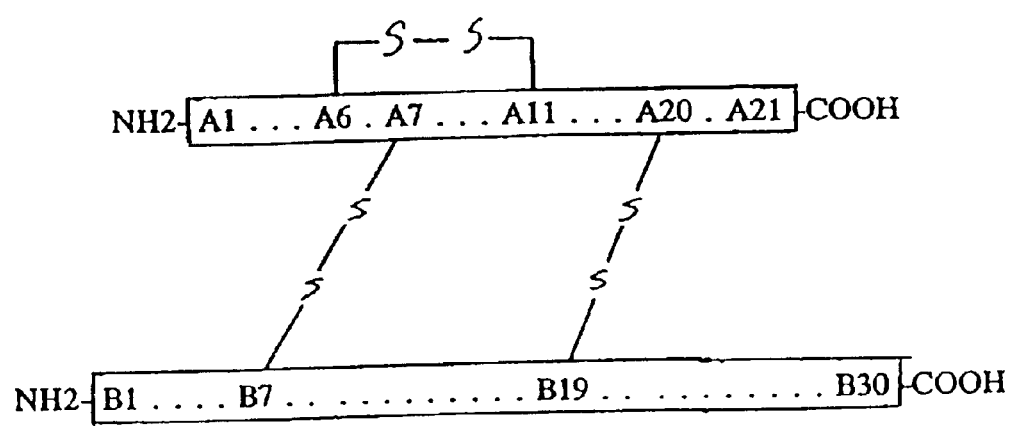

Insulin is a well-defined peptide with known amino acid sequence and structural characteristics (Watson et al., *Recombinant DNA—A Short Course*; Scientific American Books, W. H. Freeman Co., New York, 1983, pp. 231–235; Norman and Litwack, *In Hormones*, Academic Press, New York, 1987, pp. 264–317). This hormone consists of two separate peptide chains which are the A chain (21 amino acids) and the B chain (30 amino acids) joined by disulfide bridges as indicated in FIG. 1B. Proinsulin is the biological precursor of insulin and is a single peptide chain formed when the A and B chains are connected by the C peptide (FIG. 1A).

1.2.4. Human Insulin Produced by Recombinant Methods

Human insulin was the first animal protein made in bacteria in a sequence identical to that of the human pancreatic peptide (Watson et al., *Recombinant DNA—A Short Course*: Scientific American Books, W. H. Freeman Co., New York, 1983, pp. 231–235). The first successful expression of human insulin in laboratory was announced in 1978 and human insulin was approved as a therapeutic drug in 1982 (Johnson, *Science*, 1983, 219:632–637).

1.2.4.1. Two-Chain Method

According to this method, each insulin chain is produced as a β-galactosidase (β-gal) fusion protein in separate fermentations using *E. Coli* transformed with plasmids containing a DNA sequence encoding the A or B chain of human insulin, respectively. The products are intracellular and appeared in prominent cytoplasmic inclusion bodies (Williams et al., *Science*, 1982, 215(5):687–689). Recombinant proteins produced in *E. Coli* usually represent 10–40% of the total protein (Burgess, *Protein Engineering*; Oxender, D. L., Fox, C. F., Eds.; Alan R. Liss, Inc.; New York, 1987; pp. 71–82.).

Once removed from the inclusion bodies, chemical cleavage by CNBr at the Met residue between the β-galactosidase and the A or B chain, followed by purification, gave separate A and B peptides. The peptides are then combined and induced to fold at a ratio of 2:1 of A–B chain (S-sulfonated forms) in the presence of limited amounts of mercaptan in order to obtain an active hormone (Chance et al., *In Peptides: Synthesis-Structure-Function*, Rich D. M. Gross, E., Eds., Pierce Chemical Co., Rockford, Ill. 1981, pp.721–728, Frank and Chance, *In Quo Vadis? Therapeutic Agents Produced by Genetic Engineering*, Joyesuk et al., Eds., Sanoff Group, Toulouse-Labege, France, 1985, pp. 137–148). After 24 h, the yield is approximately 60% based on the amount of B chain used (Chance et al. *In Insulins, Growth Hormone and Recombinant DNA Technology*, Raven Press, New York.

1981, pp. 71–85; Johnson, *Fluid Phase Equilib.*, 1986, 29: 109–123). Goeddel et al., *Proc. Natl. Acad. Sci. U.S.A.*, 1979, 76(1):106–110, obtained similar results with 20% of the total cellular protein expressed as either the A or B chain fusion protein. Subsequent folding of S-sulfonated chains give 50–80% correct folding.

The large size of the β-gal fusion protein limits yields since the fusion protein of β-gal (~1000 amino acids) and insulin A or B chain (21 or 30 amino acids, respectively) became detached from the cell's ribosome (premature chain termination during translation and therefore yields incomplete insulin peptides (Burnett, *Experimental Manipulation of Gene Expression*, Inouye, Ed., Academic Press, New York, 1983, pp. 259–277; Hall. *Invisible Frontiers—The Race to Synthesize a Human Gene*, Atlantic Monthly Press, New York, 1987). A key improvement to this approach is the use of the tryptophan (Trp) operon in place of the lac operon (β-gal system) to obtain a smaller fusion protein. The Trp operon consists of a series of five bacterial genes which sequentially synthesize the enzymes responsible for the anabolism of tryptophan. One of these enzymes, Trp E, has only 190 amino acids compared to β-gal's 1000 amino acids. The Trp E gene followed by genes for the A or B chains of insulin has the added advantage of enhancing fusion protein production from 5–10% to 20–30% of the total protein (Hall, *Invisible Frontiers—The Race to Synthesize a Human Gene*, Atlantic Monthly Press, New York, 1987) since the Trp promoter is a strong promoter in *E. Coli*. This leads to at last 10-fold greater expression of polypeptide when compared to the lac (i.e., β-gal) system (Burnett, *Experimental Manipulation of Gene Expression*, Inouye, Ed., Academic Press, New York, 1983, pp. 259–277). The Trp operon is turned on when the *E. Coli* fermentation runs out of tryptophan (Hall, *Invisible Frontiers—The Race to Synthesize a Human Gene*, Atlantic Monthly Press, New York. 1987; Etienne-Decent, *In Genetic Biochemistry: From Gene to Protein*, Ellis Horwood Limited, Chichester, U.K., 1988, pp. 125–127). This characteristic is beneficial during fermentation since cell mass can first be maximized. Then, when appropriate, the cell's insulin production system can be turned on by allowing the fermentation media to become depleted in Trp.

After fermentation is completed, the cells are recovered and disrupted. The cell debris is than separated from the inclusion bodies, and the inclusion bodies are dissolved in a solvent, although specifics are not known (Wheelwright, *Protein Purification*, Oxford University Press; New York, 1991, p. 217). Inclusion bodies are sometimes dissolved in 6 M guanidine HCl and 0.1 mM dithiothreitol (Burgess, *Protein Engineering*, Oxender and Fox, Eds., Alan R. Liss, Inc., New York, 1987, pp. 71–82). Next, the Trp-LE-Met-A chain and the Trp-LE-Met-B chain undergo a CNBr cleavage to release the A and B insulin chains. Further modifications of the A and B chains include oxidative sulfitolysis, purification and combination to produce crude insulin. This crude insulin is subjected to ion exchange, size exclusion, and reversed-phase high-performance liquid chromatography (RP HPLC) to produce the purified recombinant human insulin (Frank and Chance, *Munch Med. Wschr.* 1983, 125(Suppl. 1):514–520).

1.2.4.2. Proinsulin Method (Intracellular)

Human insulin can also be made with recombinant microorganisms that produce intact proinsulin instead of the A or B chains separately (Kroeff et al., *J. Chromatogr*, 1989, 481:45–61). Initially, mRNA is copied into cDNA, and a methionine codon is chemically synthesized and attached to the 5' end of the proinsulin cDNA. The cDNA is inserted into a bacterial gene in a plasmid vector that is introduced and then grown in *E. Coli*. Proinsulin can be released from the bacterial enzyme (β-gal) fragment (or alternatively from the Trp-LE/Met Proinsulin (Trp proinsulin) by destroying the methionine linker. The proinsulin chain is subjected to a folding process to form the correct intramolecular disulfide bridges, and the C peptide can then be cleaved with enzymes to yield human insulin (Frank and Chance, *Munch Med. Wschr.*, 1983, 125(Suppl. 1):514–520). In comparison, the two-chain method previously described is more complex.

Dorschug et al. constructed recombinant plasmid encoding fusion proteins containing a mini-proinsulin (B-Arg-A), expressed the fusion proteins in *E.coli* (inclusion body) and yeast (secreted), prepared correctly folded mini-proinsulin via BrCN cleavage and oxidative sulfitolysis, and converted the correctly folded mini-proinsulin into human insulin by treatment with trypsin and carboxypeptidase B (EP 0,347, 781 B1; IL 9,562,511 B and AU 611,303 B2).

Tottrup and Carlsen, *Biotechnol. Bioeng*, 1990, 35:339–348 used the yeast system in an optimized batch-fed fermentation, yields of the fusion protein of superoxide dismutase-human proinsulin (SOD-PI) were reported to be 1500 mg/L. SOD-PI would be the starting material for the production of recombinant human insulin; yields of the final product have not been reported.

Recently, Castellanos-Serra et al., *FEBS Letters*, 1996, 378:171–176 expressed in *E. Coli* a proinsulin fusion protein carrying a modified interleukin-2 N-terminal peptide (1–22 amino acid residues) linked to the N-terminus of proinsulin by a lysine residue. The chimeric proinsulin was isolated from inclusion bodies, refolded via oxidative sulfitolysis, and then converted into the correctly fusion proteins insulin by prolonged reaction with trypsin and carboxypeptidase B. The IL2-proinsulin fusion can be folded correctly without first removing the IL2 fragment, thus eliminating the cyanogen bromide and the associated purification steps. However, the step of oxidative sulfitolysis and the associated purification steps cannot be avoided by the use of IL2-proinsulin fusion protein.

1.2.4.3. Proinsulin Method (Secreted)

Villa-Komaroff et al., *Proc. Natl. Acad. Sci. U.S.*, 1978, 75(8):3727–3731 were first to describe a secretion system for human proinsulin in *E. Coli*. Thim et al. constructed recombinant plasmids encoding fusion proteins containing a modified yeast mating factor α I leader sequence and an insulin precursor (Thim et al., *Proc. Natl. Acad. Sci. USA*, 1986, 83:6766–6770). The leader sequence serves to direct the fusion protein into the secretory pathway of the yeast cell and to expose the fusion protein to the Lys-Arg processing enzyme system. Partial processing also occurred at one or both dibasic sequences between B and A chains within proinsulin and other insulin precursors containing a short spacer peptide (containing 6 or more amino acid residues) in place of the C peptide. In contrast, no processing was observed in the absence of a spacer peptide in the insulin precursor molecule, e.g. B-Arg-Arg-A (where A and B are the A and B chain of human proinsulin, respectively). This type of single-chain insulin precursors could enzymatically be converted into insulin by treatment with trypsin and carboxypeptidase B Diers et al., *Drug Biotechnology Regulations (Scientific Basis and Practices)*, Chiu and Gueriguian, Eds., Marcel Dekker, Inc., New York, 1991, pp. 167–177, describe the unfolded peptide as a leader or prosegment, next a Lys-Arg sequence, the B chain (amino acids 1–29), a short peptide bridge, followed by the A chain (amino acids 1–21). In this precursor, amino acid 29 of the B chain of insulin is connected to amino acid 1 of the A chain by a short connecting peptide containing one basic amino acid adjacent to the A chain. Human insulin is produced through transpeptidation followed by hydrolysis of the ester bond formed. Several chromatography steps follow for further purification.

1.2.5. Folding of Insulin Precursors

Human insulin is a protein possessing two amino acid chains of 51 amino acid residues in all. Six cysteine residues are present in the two amino acid chains, which in each case two cysteine residues being linked to each via a disulfide bond. Statistically, there are 15 possibilities of forming disulfide bridges within one human insulin molecule. However, only one of the 15 possibilities exists in biologically active human insulin with the following disulfide bridges: 1) A6–A11; 2) A7–B7; and 3) A20–B19.

The formation of the disulfide bridges which are present in human insulin is effected by way of an intermediate, with the cysteine residues of the human insulin being provided with a sulfur protective group, e.g., with a S-sulfonate ($-S-SO_3^-$) group (EP 0,037,255). In addition, pig proinsulin in which the cysteine residues are present as thio residues (—SH) has been used to obtain proinsulin possessing correctly linked cysteine bridges (*Biochemistry*, 1968, 60:622–629). Obermeier et al. described a process for obtaining proinsulin possessing correctly linked cysteine bridges from a corresponding proinsulin amino acid chain at a concentration of 0.05 to 0.3 g per liter in the presence of mercaptan, chaotropic auxiliary agents and hydrophobic absorber resins (U.S. Pat. No. 5,473,049). The step of oxidative sulfitolysis is eliminated in the process described in U.S. Pat. No. 5,473,049. However, the insulin protein can only be folded at a low concentration, which greatly diminishes the commercial value of this process. In addition, the use of large amount of mercaptan and hydrophobic absorber resins increase process complexity and down-stream purification costs. From the disclosure of the U.S. Pat. No. 5,473,049, it is unclear whether the benefit of eliminating the step of oxidative sulfitolysis step will outweigh the increased down-stream purification costs.

Citation of references hereinabove shall not be construed as an admission that such references are prior art to the present invention.

2. SUMMARY OF THE INVENTION

The present invention relates to a chimeric protein comprising, from N-terminus to C-terminus: a) a first peptidyl fragment consisting of an amino acid sequence that has at least 40% identity to a domain containing at least first 20 N-terminal amino acids of human growth hormone (hGH) protein, in which the percentage identity is determined over an amino acid sequence of identical size to the domain of hGH; b) an Arg residue, or a Lys residue, or a second peptidyl fragment consisting of it least 2 amino acids in which peptidyl fragment the most C-terminal amino acid residue is an Arg or a Lys; and c) a third peptidyl fragment consisting of an amino acid sequence containing more than two cysteine (Cys) residues which peptidyl fragment is not a portion of hGH protein. In particular, the invention relates to a chimeric protein wherein the third peptidyl fragment is an insulin precursor.

The invention also relates to a process for obtaining a first correctly folded insulin-precursor-containing chimeric protein comprising contacting an incorrectly folded second insulin-precursor-containing chimeric protein, which said second insulin-precursor-containing chimeric protein consists of an intramolecular chaperone (IMC) like peptidyl fragment separated from the insulin precursor by one or more cleavable amino acid residues, with at least one chaotropic auxiliary agent in an aqueous medium; wherein said IMC like peptidyl fragment: a) contains from about 20 to about 200 amino acid residues; b) is not the insulin precursor or a portion thereof; and c) improves the insulin precursor folding such that the yield of the correctly folded first insulin-precursor-containing chimeric protein when the incorrectly folded second insulin-precursor-containing chimeric protein is contacted with the chaotropic auxiliary agent is higher than the yield of the correctly folded insulin precursor when the incorrectly folded insulin precursor, which does not contain said IMC like peptidyl fragment, is contacted with the same chaotropic auxiliary agent.

The present invention further relates to an assay for screening an amino acid sequence for the ability to improve folding of an insulin precursor, comprising: (a) changing the amino acid sequence of the first peptidyl fragment of a chimeric protein disclosed in Section 4.2, which contains an insulin precursor, obtaining said chimeric protein with said changes, contacting said chimeric protein with said changes with at least one chaotropic auxiliary agent in an aqueous medium under conditions and for a time sufficient such that said chimeric protein folds correctly, and measuring the folding yield of said chimeric protein with said changes; (b) obtaining the chimeric protein used in step (a), but without any amino acid sequence changes described in step (a), contacting the chimeric protein without any amino acid sequence changes described in step (a) with the same chaotropic auxiliary agents used in step (a) in an aqueous medium under the same conditions and for a same time used in step (a), and measuring the folding yield of the chimeric protein; and (c) comparing the folding yield of the chimeric proteins measured in step (a) and (b), respectively, in which the yield measured in step (a) substantially equals or is greater than the yield measured in step (b) indicates that the amino acid sequence improves folding of the insulin precursor.

3. BRIEF DESCRIPTION OF THE DRAWINGS

FIGS. 1A and 1B. Structure of proinsulin and mature insulin with correctly formed disulfide bridges. 1A depicts the structure of proinsulin. 1B depicts the structure of mature insulin with correctly formed disulfide bridges.

Figure 2:
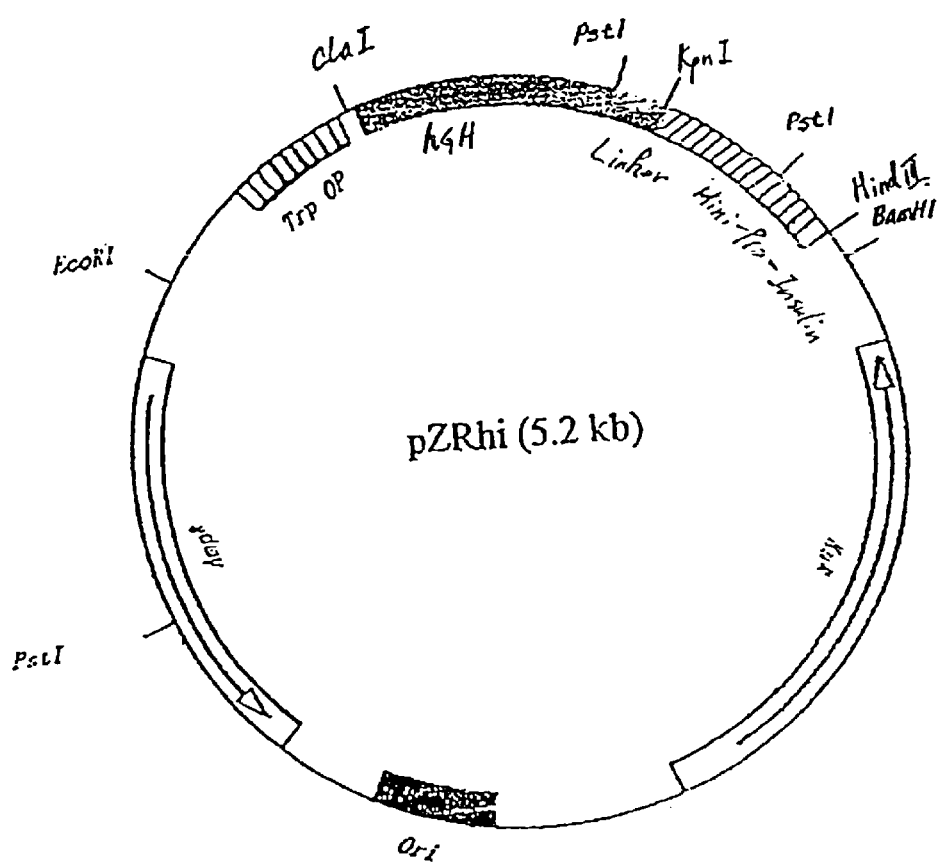

FIG. 2. Map of the hGH-mini-proinsulin (SEQ ID NO:6) expression vector (pZRhi-1).

4. DETAILED DESCRIPTION OF THE INVENTION

Recombinant processes make it possible to produce human proinsulin, or proinsulin with an amino acid sequence and/or amino acid chain length diverging from that of a natural human insulin, in microorganisms. One major problem in the production of human proinsulin or its derivatives in microorganisms such as *E. coli* is the intracellular degradation (Ladisch and Kohlmann, *Biotechnol. Prog.*, 1992, 2:469478). In addition, human proinsulin or its derivatives recombinantly produced in microorganisms do not possess correctly linked cysteine bridges (U.S. Pat. No. 5,473,049).

Prior to the present invention, a known process for obtaining human insulin recombinantly is based on the following procedures: 1) fermentation of the microorganisms transformed with a vector expressing a fusion protein containing human proinsulin or its derivatives; 2) cell disruption; 3) isolation of the fusion protein; 4) cleavage of the fusion protein with cyanogen bromide; 5) isolation of the cleavage product having the proinsulin sequence; 6) oxidative sulfitolysis; 7) formation of the correctly linked cysteine bridges; 8) desalting of the proinsulin; 9) chromatographic purification of the proinsulin possessing the correctly linked cysteine bridges; 9) concentration of the proinsulin solution; 10) chromatographic purification of the concentrated proinsulin solution; 11) enzymatic cleavage of the proinsulin in order to obtain human insulin; and 12) chromatographic purification of the resulting human insulin (EP 0,055,945). Disadvantages of the this process are the numerous procedural steps and the losses in the purification steps, which lead to a low yield of insulin. From the step of the isolated fusion protein via cyanogen bromide cleavage, sulfitolysis and purification of the proinsulin, a loss of proinsulin of up to 40% is to be expected (EP 0,055,945). On the other hand, the yield of recombinantly producing insulin, or its derivatives, can be significantly increased if the number of the necessary procedural steps are significantly reduced.

One objective of the present invention was to develop a recombinant process for obtaining human insulin with correctly linked cysteine bridges with fewer necessary procedural steps, and hence resulting higher yield of human insulin. Another objective of the present invention was to develop an insulin-precursor-containing chimeric protein that can be used in the above process. Still another objective of the present invention was to develop an assay for screening an amino acid sequence, when linked to an insulin precursor via peptidyl bond, will improve folding of the insulin precursor.

Applicants have searched for peptide sequences that would not only protect insulin sequences from the intracellular degradation by microorganism host, but also, compared to the then existing human insulin expression system, possess the following advantages: when linked to an insulin precursor via peptidyl bond, 1) promotes the folding of the fused insulin precursor; 2) facilitates the solubility of the fusion protein and decrease the intermolecular interactions among the fusion proteins, thus allowing folding of the fused insulin precursor at a commercially significant high concentration; 3) eliminates the procedural steps of cyanogen bromide cleavage, oxidative sulfitolysis and the related purification steps; and 4) eliminates the use of high concentration of mercaptan or the use of hydrophobic absorbent resins.

Applicant found, surprisingly, that linking an IMC like sequence to an insulin precursor via one or more cleavable amino acid residues accomplish the objectives of the present invention. The IMC like sequence has certain characteristics of an IMC sequence such as helping the target protein folding, containing higher percentage of charged amino acid residues than its target protein, having polarized distribution of the charged amino acid residues and having a sequence that appears to be "tailor-made" for the target protein. However, the IMC like sequence used in present invention is different from an IMC sequence in several key aspects. First, the IMC like sequence is heterogeneous to the target protein. i.e., not a propeptide of the target protein. For example, if an insulin precursor is a target protein to be folded, an IMC like sequence is not the insulin precursor or a portion thereof. In addition, the size of the IMC like sequence is from about 20 to about 200 amino acid residues.

Additionally, contrary to the teaching in the prior art (Castellanos-Serra et al., *FEBS Letters*, 1996, 378:171–176), Applicant found, surprisingly, that including, within the IMC like sequence, one or more cleavable amino acid residues which are identical to the one or more cleavable amino acid residues that separate the IMC like sequence and an insulin precursor allows fragmented removal of the IMC like sequence after folding, hence, simplifying down-stream purification steps.

For clarity of disclosure, and not by way of limitation, the detailed description of the invention is divided into the subsections which follow.

4.1. Nucleic Acids Encoding the Chimeric Protein Disclosed in Section 4.2

The present invention provides an isolated nucleic acid comprising a nucleotide sequence encoding the chimeric protein disclosed in Section 4.2.

In a specific embodiment, the present invention provides an isolated nucleic acid comprising a nucleotide sequence encoding the chimeric protein having the amino acid sequence of SEQ ID NO:6.

In another specific embodiment, the present invention provides an isolated nucleic acid comprising a nucleotide sequence encoding the chimeric protein having the amino acid sequence of SEQ ID NO:7.

In a preferred embodiment, the present invention provides an isolated DNA molecule comprising a nucleotide sequence encoding the chimeric protein disclosed in Section 4.2.

In another preferred embodiment, the present invention provides an isolated nucleic acid comprising a nucleotide sequence complementary to the nucleotide sequence encoding the chimeric protein disclosed in Section 4.2.

In still another specific embodiment, the present invention provides an isolated nucleic acid hybridizable to the nucleotide sequence encoding the first, second and third peptidyl fragments of the DNA encoding the chimeric protein disclosed in Section 4.2.

The nucleic acid comprising a nucleotide sequence encoding the chimeric protein disclosed in Section 4.2., or any fragments, analogues or derivatives thereof, can be obtained by any method(s) known in the art. The nucleic acid may he chemically 35 synthesized entirely. Alternatively, the nucleic acid encoding each fragment of the chimeric protein, i.e., the first, second or third peptidyl fragment, may be obtained by molecular cloning or may be purified from the desired cells. The nucleic acid encoding each fragment of the chimeric protein may then be chemically or enzymatically ligated together to form the nucleic acid comprising a nucleotide sequence encoding the chimeric protein disclosed in Section 4.2., or any fragments, analogues or derivatives thereof.

Any human cell potentially can serve as the nucleic acid source for the isolation of hGH nucleic acids. Any mammalian cell potentially can serve as the nucleic acid source for the isolation of insulin nucleic acids. The nucleic acid sequences encoding insulin can be isolated from mammalian, human, porcine, bovine, feline, avian, equine, canine, as well as additional rodent or primate sources, etc.

The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from cDNA, cDNA is generated from totally cellular RNA or mRNA by methods that are well known in the art. The gene may also be obtained from genomic DNA, where DNA fragments are generated (e.g. using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once a nucleic acid comprising a nucleotide sequence encoding the chimeric protein disclosed in Section 4.2., or any fragments, analogues or derivatives thereof, has been obtained, its identity can be confirmed by nucleic acid sequencing (by any method well known in the art) and comparison to the known sequences. DNA sequence analysis can be performed by any techniques known in the art, including but not limited to the method of Maxam and Gilbert (Maxam and Gilbert, 1980, *Meth. Enzymol.*, 65:499–560), the Sanger dideoxy method (Sanger et al., 1977, *Proc. Natl. Acad. Sci. U.S.A.*, 74:5463), the use of T7 DNA polymerase (Tabor and Richardson, U.S. Pat. No. 4,795,699), use of an automated DNA sequenator (e.g., Applied Biosystems, Foster City, Calif.) or the method described in PCT Publication WO 97/15690.

Nucleic acids which are hybridizable to an nucleic acid comprising a nucleotide sequence encoding the chimeric protein disclosed in Section 4.2., or any fragments, analogues or derivatives thereof, can be isolated, by nucleic acid hybridization under conditions of low, high, or moderate stringency (See also Shilo and Weinberg, 1981, *Proc. Natl. Acad. Sci. USA*, 78:6789–6792).

4.2. Chimeric Protein

The present invention provides a chimeric protein comprising, from N-terminus to C-terminus: a) a first peptidyl fragment consisting of an amino acid sequence that has at least 40% identity to a domain containing at least first 20 N-terminal amino acids of human growth hormone (hGH) protein, in which the percentage identity is determined over an amino acid sequence of identical size to the domain of hGH; b) an Arg residue, or a Lys residue, or a second peptidyl fragment consisting of at least 2 amino acids in which peptidyl fragment the most C-terminal amino acid residue is an Arg or a Lys; and c) a third peptidyl fragment consisting of an amino acid sequence containing more than two cysteine (Cys) residues which peptidyl fragment is not a portion of hGH protein.

In a preferred embodiment, the present invention provides a chimeric protein described above, wherein the first peptidyl fragment consists of an amino acid sequence that has at least 60% identity to the domain of hGH protein.

In another preferred embodiment, the present invention provides a chimeric protein described above, wherein the first peptidyl fragment is capable of being bound by an anti-hGH antibody.

In a more preferred embodiment, the present invention provides a chimeric protein described above, wherein the first peptidyl fragment consists of the amino acid sequence of SEQ ID NO:1.

In another more preferred embodiment, the present invention provides a chimeric protein described above, wherein the first peptidyl fragment consists of the amino acid sequence of SEQ ID NO:2.

In a preferred embodiment, the present invention provides a chimeric protein described above, wherein the second peptidyl fragment consists of the amino acid sequence of SEQ ID NO:3.

In a specific embodiment, the present invention provides a chimeric protein described above, wherein the third peptidyl fragment is an insulin precursor.

In a preferred embodiment, the present invention provides a chimeric protein described above, wherein the insulin precursor is of human origin.

In a more preferred embodiment, the present invention provides a chimeric protein described above, wherein the human insulin precursor is capable of being bound by an anti-human-insulin antibody.

In another more preferred embodiment, the present invention provides a chimeric protein described above, wherein the human insulin precursor consists of the amino acid sequence of SEQ ID NO:4.

In still another more preferred embodiment, the present invention provides a chimeric protein described above, wherein in the human insulin precursor, B chain and A chain of the human insulin precursor are separated by an amino acid residue or a peptidyl fragment consisting of 2 to 34 amino acid residues.

In yet another more preferred embodiment, the present invention provides a chimeric protein described above, wherein the human insulin precursor consists of the amino acid sequence of SEQ ID NO:5.

In a more preferred embodiment, the present invention provides a chimeric protein consisting of the amino acid sequence of SEQ ID NO:6.

In another most preferred embodiment, the present invention provides a chimeric protein consisting of the amino acid sequence of SEQ ID NO:7.

4.3. Obtaining Chimeric Disclosed in Section 4.2

Chimeric proteins disclosed in Section 4.2., and derivatives, analogues and fragments thereof can be obtained by any method known in the art, including but not limited to recombinant expression methods, purification from natural sources, and chemical synthesis.

For example, chimeric proteins disclosed in Section 4.2. can be obtained by recombinant protein expression techniques. For recombinant expression, the gene or portion thereof encoding chimeric proteins disclosed in Section 4.2. is inserted into an appropriate cloning vector for expression in a particular host cell. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated gene encoding chimeric proteins disclosed in Section 4.2., cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleotide sequence coding for chimeric proteins disclosed in Section 4.2., and derivatives, analogues and fragments thereof, or a functionally active analogues or fragments or other derivatives thereof, can be inserted into an appropriate expression vector, i.e., a vector which contains the necessary elements for the transcription and translation of the inserted protein-coding sequence. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding chimeric proteins disclosed in Section 4.2., and derivatives, analogues and fragments thereof, may be regulated by a second nucleic acid sequence so that the chimeric proteins disclosed in Section 4.2. are expressed in a host transformed with the recombinant DNA molecule. For example, expression of the chimeric proteins disclosed in Section 4.2. may be controlled by any promoter/enhancer element known in the art. Promoters which may be used to control the expression of the chimeric proteins disclosed in Section 4.2. include, but are not limited to, the SV40 early promoter region (Bernoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.*, 78:1441–1445), the regulatory sequences of the metallothionein gene (Brinster et al., 1982, *Nature* 296:39–42); prokaryotic expression vectors such as the β-lactamase promoter (Villa-Kamaroff, et al., 1978, *Proc. Natl. Acad. Sci. U.S.A.*, 75:3727–3731), the tac promoter (DeBoer, et al., 1983, *Proc. Natl. Acad. Sci. U.S.A.*, 80:21–25); or Trp E promoter (Hall, *Invisible Frontiers—The Race to Synthesize a Human Gene*, Atlantic Monthly Press, New York, 1987) see also "Useful proteins from recombinant bacteria" in *Scientific American*, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648, Hammer et al., 1987, *Science* 235:53–58; alpha 1-antitrypsin gene control region which is active in the liver (Kelsey et al., 1987, *Genes and Devel.* 1:161–171), beta-globin gene control region which is active in myeloid cells (Mogram et al., 1985, *Nature* 315:338–340; Kollias et al., 1986, *Cell* 46:89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropic releasing hormone gene control region which is active in the hypothalamus (Mason et al., 1986, *Science* 234:1372–1378).

For example, a vector can be used that comprises a promoter operably linked to an nucleic acid encoding the chimeric proteins disclosed in Section 4.2., one or more origins of replication, and, optionally, one or more selectable markers (e.g., an antibiotic resistance gene).

Expression vectors containing gene inserts encoding the chimeric proteins disclosed in Section 4.2., or fragments, analogues or derivatives thereof, can be identified by three general approaches: (a) nucleic acid hybridization, (b) presence or absence of "marker" gene functions, and (c) expression of inserted sequences. In the first approach, the presence of a gene encoding the chimeric proteins disclosed in Section 4.2. inserted in an expression vector can be detected by nucleic acid hybridization using probes comprising sequences that are homologous to an inserted gene encoding the chimeric proteins disclosed in Section 4.2. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a gene encoding the chimeric proteins disclosed in Section 4.2. in the vector. For example, if the gene encoding the chimeric proteins disclosed in Section 4.2. is inserted within the marker gene sequence of the vector, recombinants containing the insert encoding the chimeric proteins disclosed in Section 4.2. can be identified by the absence of the marker gene function. In the third approach, recombinant expression vectors can be identified by assaying the chimeric proteins product expressed by the recombinant. Such assays can be based, for example, on the physical or functional properties of the chimeric proteins disclosed in Section 4.2. in in vitro assay systems, e.g., binding with anti-hGH, or anti-insulin antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered chimeric protein disclosed in Section 4.2. may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

Both cDNA and genomic sequences can be cloned and expressed.

The chimeric protein disclosed in Section 4.2., or fragments, analogues or derivatives thereof, may also be isolated and purified by standard methods including chromatography (e.g., ion exchange, affinity, and sizing column chromatography), centrifugation, differential solubility, or by any other standard technique for the purification of proteins. The functional properties may be evaluated using any suitable assay.

The nucleic acid sequence encoding the chimeric protein disclosed in Section 4.2., or fragments, analogs or derivatives thereof, can be mutated in vitro or in vivo, to create and/or destroy translation, initiation, and/or termination sequences, or to create variations in coding regions. Any technique for mutagenesis known in the art can be used, including, but not limited to, in vitro site-directed mutagenesis (Hutchinson et al., 1978, J. Biol. Chem. 253:6551), use of TAB linkers (Pharmacia), mutation-containing PCR primers, etc.

The experimentation involved in mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

In addition, the chimeric protein disclosed in Section 4.2., or fragments, analogues or derivatives thereof, can be chemically synthesized (See, e.g., Clark-Lewis et al., 1991, Biochem. 30:3128–3135 and Merrifield, 1963, J. Amer. Chem. Soc. 85:2149–2156). For example, the chimeric proteins disclosed in Section 4.2., or fragments, derivatives and analogues can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). The chimeric protein disclosed in Section 4.2., or fragment, derivatives and analogues can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49).

The chimeric proteins disclosed in Section 4.2., or fragments, derivatives and analogues thereof, may he synthesized in their entirety by the sequential addition of amino acid residues or alternatively as fragment subcomponents which may be combined using techniques well known in the art, such as, for example, fragment condensation (Shin et al., 1992, Biosci. Biotech. Biochem. 56:404408; Nyfeler et al., 1992, Peptides, Proc. 12th Amer. Pep. Soc., Smith and Rivier (eds), Leiden, pp 661–663; and Nokihara et al., 1990, Protein Research Foundation, Yanaihara (ed), Osaka, pp 315–320).

In a less preferred embodiment, the chimeric proteins disclosed in Section 4.2., or fragments, derivatives and analogues thereof, can be obtained by proteolysis of the protein followed by purification using standard methods such as those described above (e.g., immunoaffinity purification).

4.4. Obtaining Correctly Folded Insulin Precursor

The present invention provides a process for obtaining a correctly folded first insulin-precursor-containing chimeric protein comprising, contacting an incorrectly folded second insulin-precursor-containing chimeric protein, which said second insulin-precursor-containing chimeric protein consists of an intramolecular chaperone (IMC) like peptidyl fragment separated from the insulin precursor by one or more cleavable amino acid residues, with at least one chaotropic auxiliary agent in an aqueous medium; wherein said IMC like peptidyl fragment: a) contains from about 20 to about 200 amino acid residues; b) is not the insulin precursor or a portion thereof; and c) improves the insulin precursor folding such that the yield of the correctly folded first insulin-precursor-containing chimeric protein when the incorrectly folded second insulin-precursor-containing chimeric protein is contacted with the chaotropic auxiliary agent is higher than the yield of the correctly folded insulin precursor when the incorrectly folded insulin precursor, which does not contain said IMC like peptidyl fragment, is contacted with the same chaotropic auxiliary agent.

As used herein, the term "human insulin precursor" refers to a molecule which 1) contains the human insulin A chain and B chain, or analogues, derivatives and fragments thereof, 2) contains six cysteine residues, 3) has a removable connecting moiety which is joined to the insulin A chain and B chain, and 4) is capable of being bound by an anti-human-insulin antibody. Examples of human insulin precursor include, but are not limited to, the ones disclosed in Ladisch and Kohlmann, *Biotechnol. Prog.*, 1992, 8:469–478; Thim et al., *Proc. Natl. Acad. Sci. USA*. 1986, 83:6766–6770; U.S. Pat. No. 5,473,049; U.S. Pat. No. 5,457,066; and EP 0,347, 781 B1.

The term "correctly folded" human insulin precursor or insulin-precursor-containing chimeric protein refers to a molecule wherein the human insulin precursor has the conformation and disulfide bridges as found in a natural, biologically active human insulin, i.e., the disulfide bridges between a) A-6 and A-11, b) A-7 and B-7, c) A-20 and B-19, are formed. The term "incorrectly folded" human insulin precursor or insulin-precursor-containing chimeric protein refers to a molecule wherein the human insulin precursor lacks the conformation, disulfide bridges as found in a natural, biologically active human insulin, or both.

In a preferred embodiment, the present invention provides a process for obtaining a correctly folded insulin-precursor-containing chimeric protein described above, wherein the insulin precursor is of human origin. Also preferable, the human insulin precursor is capable of being bound by an anti-human-insulin antibody. Still preferably, the human insulin precursor consists of the amino acid sequence of SEQ ID NO:4. Yet preferably, in the human insulin precursor, B chain and A chain of the human insulin precursor are separated by an amino acid residue or a peptidyl fragment consisting of 2 to 34 amino acid residues. More preferably, the human insulin precursor consists of the amino acid sequence of SEQ ID NO:5.

In a preferred embodiment, the present invention provides a process for obtaining a correctly folded insulin-precursor-containing chimeric protein described above, wherein the IMC like peptidyl fragment contains higher percentage of charged amino acid residue than the insulin precursor. Also preferably, wherein in the IMC like peptidyl fragment, the N-terminal half contains more positively charged amino acid residues than negatively charged amino acid residues and the C-terminal half contains more negatively charged amino acid residues than positively charged amino acid residues. Still preferably, the IMC like peptidyl fragment consists of an amino acid sequence that has at least 40% identity to a domain containing at least first 20 N-terminal amino acids of human growth hormone (hGH) protein, in which the percentage identity is determined over an amino acid sequence of identical size to the domain of hGH. Yet preferably, the IMC like peptidyl fragment consists of an amino acid sequence that has at least 60% identity to a domain containing at least first 20 N-terminal amino acids of human growth hormone (hGH) protein. Yet preferably, the IMC like peptidyl fragment is capable of being bound by an anti-hGH antibody. More preferably, the IMC like peptidyl fragment consists of the amino acid sequence of SEQ ID NO:1. Also more preferably, the IMC like peptidyl fragment consists of the amino acid sequence of SEQ ID NO:2.

In a preferred embodiment, the present invention provides a process for obtaining a correctly folded insulin-precursor-containing chimeric protein described above, wherein the cleavable amino acid residue is an Arg or a Lys residue. Also preferably, the cleavable amino acid residues consist of the amino acid sequence of SEQ ID NO:3.

In a specific embodiment, the present invention provides a process for obtaining a correctly folded insulin-precursor-containing chimeric protein described above, wherein in the incorrectly folded second insulin-precursor-containing chimeric protein, the IMC like peptidyl fragment is located at the N-terminus of said chimeric protein. In another such specific embodiment, the IMC like peptidyl fragment is located at the C-terminus of said chimeric protein. In still another such specific embodiment, the IMC like peptidyl fragment is located between the B chain and A chain of the insulin precursor.

In a preferred embodiment, the present invention provides a process for obtaining a correctly folded insulin-precursor-containing chimeric protein described above, wherein the IMC like peptidyl fragment contains one or more cleavable amino acid residues which are identical to the one or more cleavable amino acid residues that separate the IMC like peptidyl fragment and the insulin precursor in the second insulin-precursor-containing chimeric protein. More preferably, the cleavable amino acid residue is an Arg or a Lys residue.

In a most preferred embodiment, the present invention provides a process for obtaining a correctly folded insulin-precursor-containing chimeric protein described above, wherein the incorrectly folded second insulin-precursor-containing chimeric protein consists of the amino acid sequence of SEQ ID NO:6. Also most preferably, the incorrectly folded second insulin-precursor-containing chimeric protein consists of the amino acid sequence of SEQ ID NO:7.

Chaotropic auxiliary agents are compounds which break hydrogen bonds in aqueous solution. In a specific embodiment, the present invention provides a process for obtaining a correctly folded insulin-precursor-containing chimeric protein described above, wherein the chaotropic auxiliary agent is selected from the group consisting of guanidine hydrochloride, ethylene carbonate, thiocyanate, dimethyl sulfoxide and urea. Preferably, the chaotropic auxiliary agent is urea. More preferably, the urea is present at a concentration from about 2.0 to about 8.0 M. Most preferably, the urea is present at a concentration from about 3.0 to about 6.0 M.

In another specific embodiment, the present invention provides a process for obtaining a correctly folded insulin-precursor-containing chimeric protein described above, wherein the incorrectly folded second insulin-precursor-containing chimeric protein is contacted with at least one chaotropic auxiliary agent in an aqueous medium at a pH from about 8.0 to about 10.5 and at a concentration of the incorrectly folded second insulin-precursor-containing chimeric protein from about 0.05 to about 15.0 g per liter. Preferably, the pH is maintained from about 9.0 to about 10.0. Also preferably, the incorrectly folded second insulin-precursor-containing chimeric protein is present from about 0.5 to about 5.0 g per liter. More preferably, the incorrectly folded second insulin-precursor-containing chimeric protein is present from about 2.0 to about 3.0 g per liter.

Mercaptans are compounds which are soluble in water and contain at least one —SH group. In still another specific embodiment, the present invention provides a process for obtaining a correctly folded insulin-precursor-containing chimeric protein described above, further comprising contacting the incorrectly folded second insulin-precursor-containing chimeric protein with a quantity of a mercaptan, which quantity yields less than 5 —SH radical of the mercaptan per cysteine residue of the incorrectly folded second insulin-precursor-containing chimeric protein. In yet another specific embodiment, the incorrectly folded second insulin-precursor-containing chimeric protein is contacted with the mercaptan and the chaotropic auxiliary agent concurrently. In yet another specific embodiment, the incorrectly folded second insulin-precursor-containing chimeric protein is contacted with the mercaptan and the chaotropic auxiliary agent sequentially. Preferably, the quantity of the mercaptan yields from about 0.07 to about 1.0 —SH radical of the mercaptan per cysteine residue of the incorrectly folded second insulin-precursor-containing chimeric protein. Also preferably, the mercaptan is selected from the group consisting of dithiothreitol, dithioerythrol, 2-mercaptoethanol, cysteine, methyl thioglycolate, 3-mercapto-1,2-propanediol and 3-mercaptopropionic acid. More preferably, the mercaptan is 2-mercaptoethanol.

In yet another specific embodiment, the present invention provides a process for obtaining a correctly folded insulin-precursor-containing chimeric protein described above, further comprising separating the correctly folded first insulin-precursor-containing chimeric protein from the incorrectly folded second insulin-precursor-containing chimeric protein. Preferably, the first insulin-precursor-containing chimeric protein is separated from the second insulin-precursor-containing chimeric protein by ultrafiltration. More preferably, the ultrafiltration is carried out al a pH from about 8.0 to about 11.0. Most preferably, the ultrafiltration is carried out at a pH from about 9.0 to about 10.0.

In yet another specific embodiment, the present invention provides a correctly folded insulin-precursor-containing chimeric protein obtained by the process described above.

4.5. Screening an Amino Acid Sequence that Improves Folding of an Insulin Precursor The present invention provides an assay for screening an amino acid sequence for the ability to improve folding of an insulin precursor, comprising: (a) changing the amino acid sequence of the first peptidyl fragment of a chimeric protein disclosed in Section 4.2., obtaining said chimeric protein with said changes, contacting said chimeric protein with said changes with at least one chaotropic auxiliary agent in an aqueous medium under conditions and for a time sufficient such that said chimeric protein folds correctly, and measuring the folding yield of said chimeric protein with said changes; (b) obtaining the same chimeric protein used in step (a), but without any amino acid sequence changes described in step (a), contacting the chimeric protein without any amino acid sequence changes described in step (a) with the same chaotropic auxiliary agent(s) used in step (a) in an aqueous medium under the same conditions and for a same time used in step (a), and measuring the folding yield of the chimeric protein; and (c) comparing the folding yield of the chimeric proteins measured in step (a) and (b), respectively, in which the yield measured in step (a) substantially equals or is greater than the yield measured in step (b) indicates that the amino acid sequence improves folding of the insulin precursor.

The amino acid sequence of the first peptidyl fragment of a chimeric protein disclosed in Section 4.2. can be changed by any mutagenesis techniques known in the art, preferable by mutagenesis techniques described in Section 4.3.

In a preferred embodiment of the above assay, the chimeric protein consists of the amino acid sequence of SEQ ID NO:6.

In another preferred embodiment of the above assay, the chimeric protein consists of the amino acid sequence of SEQ ID NO:7.

In still another preferred embodiment of the above assay, the chaotropic auxiliary agent is urea.

In yet another preferred embodiment of the above assay, the assay further comprises contacting the chimeric protein, in step (a) and (b) respectively, with a quantity of a mercaptan, which quantity yields less than 5 —SR radical of the mercaptan per cysteine residue of the chimeric protein. More preferably, the mercaptan is 2-mercaptoethanol.

In a specific embodiment, the product of the above assay is provided.

5. EXAMPLE

A DNA fragment encoding the hGH-mini-proinsulin consisting of the amino acid sequence of SEQ ID NO:6 was chemically synthesized. The DNA fragment was cloned into a bacterial expression vector under the control of a Trp promotor. The expression vector containing the hGH-mini-proinsulin was transformed into E.coli PR1 strain and the recombinant cells were cultured in M9-CA media in the presence of trace elements. The hGH-mini-proinsulin fusion proteins were recovered from inclusion bodies and folded under the condition such that, within the folded hGH-mini-proinsulin fusion proteins, disulfide bridges were formed as they would be formed in a correctly folded human proinsulin, i.c., the disulfide bridges of A6–A11, A7–B7 and A20–B19 were formed. The folded hGH-mini-proinsulin fusion proteins were separated from the unfolded fusion proteins by a 100K ultrafiltration. The isolated, correctly folded hGH-mini-proinsulin fusion proteins were digested with trypsin to form correctly folded Arg(B31)-human-insulin. The Arg(B31)-human-insulin was purified by cation exchange chromatographies to at least 90% pure. The purified Arg(B31)-human-insulin was then digested with carboxypeptidase B to form the correctly folded human insulin, which was subsequently purified by reversed phase HPLC. The pure human insulin thus produced was characterized by N-terminal sequence analysis, molecular weight determination and peptide mapping.

5.1. Construction of hGH-Mini-Proinsulin Expression Vector

A DNA fragment encoding the hGH-mini-proinsulin consisting of the amino acid sequence of SEQ ID NO:6 was chemically synthesized according to the procedure disclosed in Gan et al., Gene, 1989, 79:159–166. A 5' Cla I site and a 3' Hind III site were included in the synthesized DNA fragment. Briefly, a fragment from the 5' Cla I to 3' Kpn I, which cuts the nucleotide sequence encoding amino acid residues 51 and 52 of the SEQ ID NO:6, and a fragment from 5' Kpn I to 3' Hind III were chemically synthesized and subcloned into a pUC18 vector, respectively. Subsequently, the DNA fragment encoding the entire amino acid sequence of SEQ ID NO:6 was subcloned into a modified pATH2 vector such that expression of the hGH-mini-proinsulin was under the control of a Trp promoter and a SD sequence. The resulting vector, pZRhi-1 (FIG. 2) was used to express the hGH-mino proinsulin fusion protein.

5.2. Expression of hGH-Mini-Proinsulin Fusion Protein

The hGH-mini-proinsulin fusion protein expression vectors were transformed into E.coli strain RR1 or K12 W3110. The transformed E.coli cells were cultured in M9-CA media in the presence of trace elements. The expression level of the hGH-mini-proinsulin fusion proteins was determined in both shaking flask and fermentor. In both cases, a high level expression, amounting to 20–25% of total E.coli proteins, was observed.

5.3. Refolding of the hGH-Mini-Proinsulin Fusion Protein

The hGH mini-proinsulin fusion proteins were expressed as an insoluble form termed "inclusion bodies". To release inclusion bodies, the *E coli* cells were disrupted by high pressure homogenizer at 800 bar. The cell debris and soluble *E.coli* proteins were removed by a centrifugation at 10,000 g. The inclusion body pellets containing the hGH-mini-proinsulin fusion proteins were washed 3 times with water. The resulting inclusion body pellets, in which the hGH-mini-proinsulin fusion proteins was about 90% pure, was used as starting material for folding. The inclusion body was dissolved in 8 M urea, pH 10.4, at a hGH-mini-proinsulin fusion protein concentration of 20–30 mg/ml in the presence of 2 to 6 mM -mercaptoethanol. The insoluble material was removed by centrifugation. The supernatant was diluted 10 fold by low concentration urea to reach a final concentration of urea from 3 to 6 M, pH 9 to 10, and of -mercaptoethanol from 0.2 to 0.6 mM. The routine folding was carried out at 4° C. at a urea concentration of 3.2 M, pH 9.3. The folding process was monitored by a C4 reverse phase HPLC with a 30–47% acetonitrile gradient in 0.1% phosphate buffer. Under such chromatographic conditions, the retention time of the correctly folded hGH-mini-proinsulin was around 23 min. The folding can be finished within 24 hr. The refolding yield was about 70%.

The folding mixture was fractionated by a 100K ultrafiltration. The correctly folded hGH-mini-proinsulin fusion proteins found in the filtrate fractions were concentrated by a 10 K ultrafiltration system. Urea was removed with water at pH 3.5. The yield of the ultrafiltration steps was over 85%.

5.4. Tryptic Cleavage of Correctly Refolded hGH-Mini-Proinsulin

For tryptic cleavage, the concentration of the correctly folded hGH-mini-proinsulin fusion protein was present from about 10–12 mg/ml, preferably at 10 mg/ml. The ratio between trypsin and the hGH-mini-proinsulin fusion protein was ranged from about 1:60 to about 1:250, preferably at 1:100. pH was maintained from about 10 to about 11, preferably at 10.8. The cleavage was allowed to proceed at 4° C. from about 1 to about 5 hr, preferably carried out for about 3.5 hr. The cleavage reaction was stopped by adjusting pH to 3.5 with phosphate buffer. Reverse phase HPLC analysis indicated that the yield for this cleavage step was more than 95%. At pH above 10, trypsin acts on the following Arg residues: the Arg residue between human mini-proinsulin B and A chains, the Arg residue between the hGH fragment and the mini-proinsulin fragment, the Arg residues within the hGH fragment. The trypsin digestion yielded several small pieces from the hGH fragment, and a human insulin with a extra Arg at C-terminus of B chain, which is termed as Arg(B31)-human-insulin. The Arg (B22) residue of human insulin was not cleaved under the above conditions, presumably due to the hindrance by three dimension structure.

The Arg(B31)-human-insulin was purified by cation exchange chromatographies using NaCl as eluent in the presence of 10 mM citrate buffer. The purified Arg(B31)-human-insulin was more than 90% pure.

5.5. Conversion of Arg(B31)-Human-Insulin to Human Insulin

The Arg(B31) at the C-terminus of the Arg(B31)-human-insulin was removed by carboxypeptidase B. The concentration of the correctly folded Arg(B3 1)-human-insulin was present at about 10 mg/ml. The ratio between carboxypeptidase B and the Arg(B31)-human-insulin was maintained at about 1:1000. The cleavage was allowed to proceed at 37° C. for about 1 hr in 50 mM Tris-HCl buffer, pH 8.0. The cleavage reaction was stopped by adjusting pH to 3.5 with phosphate buffer. The yield of human insulin was more than 99%.

5.6. Purification of Human Insulin

Human insulin produced from the carboxypeptidase B digestion was loaded onto a C8 reverse phase HPLC column that has been equilibrated with 0.1% phosphate buffer, pH 3.0. Human insulin was eluted by an acetonitrile gradient from 17% to 35% in 0.1% phosphate buffer, pH 3.0. Insulin fractions were pooled and acetic acid was added to reach a concentration of 0.125 to 0.2 M, pH 6.0. Insulin thus produced was crystallized at 4° C. The purity of the human insulin was over 99%.

5.7. Characterization of the Purified Human Insulin

The first 15 N-terminal amino acids of the purified human insulin and the WHO standard human insulin were determined by standard Edman degradation. The N-terminal sequences of both A and B chains of the purified human insulin are identical to that of the WHO standard human insulin.

The molecular weight of the purified human insulin and that of the WHO standard human insulin was determined by VG Platform mass spectrometry analysis. Both samples gave a M/Z of 5807.7.

Both the purified human insulin and the WHO standard human insulin were digested with V8 protease. The digested fragments were analyzed by C18 reverse phase HPLC. Both samples gave identical peptide mapping pattern (See Thim et al., Genetics and Molecular Biology of Industrial Microorganisms, Hershberger et al., Ed. American Society for Microbiology, 1989, p322–328).

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A chimeric protein comprising from N-terminus to C-terminus:
    an N-terminal first peptidyl fragment of from 20 amino acids in length to 92 amino acids in length and having an amino acid sequence which is identical to an N-terminal amino acid sequence of SEQ ID NO:2 of the same length as the first peptidyl fragment or having an amino acid sequence which differs by one or two residues from the N-terminal sequence of SEQ ID NO:2 of the same length;
    an arginine or lysine residue or at least one cleavable peptidyl fragment;
    a human insulin precursor peptidyl fragment consisting of a human insulin precursor which exhibits insulin-like bioactivity when folded in a bioactive conformation, and wherein the human insulin precursor peptidyl fragment comprises the A chain and the B chain of human insulin, and wherein the A chain and the B chain are separated by a removable peptidyl moiety of between 1 and 34 residues in length; and
    wherein the arginine or lysine residue or the at least one cleavable peptidyl fragment links the first peptidyl fragment and the human insulin precursor peptidyl fragment; and
    wherein the first peptidyl fragment is capable of mediating, upon contacting of the chimeric protein with a chaotropic agent, the formation of a correctly folded conformation of the human insulin precursor peptidyl fragment.

2. The chimeric protein according to claim 1, wherein the amino acid sequence of the first peptidyl fragment is an amino acid sequence of SEQ ID NO: 2 of the same length as the first peptidyl fragment.

3. The protein according to claim 2, wherein the amino acid sequence of the human insulin precursor peptidyl fragment is the amino acid sequence of SEQ ID NO:4.

4. The protein according to claim 2, wherein the amino acid sequence of the human insulin precursor peptidyl fragment is the amino acid sequence of SEQ ID NO:5.

5. The chimeric protein of claim 2, wherein the protein consists of the first peptidyl fragment; the insulin precursor peptidyl fragment; and an arginine or lysine residue or the at least one cleavable peptidyl fragment; and wherein the at least one cleavable peptidyl fragment is at least 2 amino acids in length and has a C-terminal amino acid residue selected from the group consisting of Arg and Lys.

6. The chimeric protein of claim 2, wherein the first peptidyl fragment and the insulin precursor peptidyl fragment are linked by only one amino acid residue which is an arginine or lysine residue.

7. The chimeric protein of claim 1, wherein the chimeric protein is identical in amino acid sequence to the amino acid sequence of SEQ ID NO:6 or of SEQ ID NO:7.

8. A method for preparing a protein having a correctly folded human insulin precursor, said method comprising:
   expressing a recombinant protein comprising, from N-terminus to C-terminus,
      a first peptidyl fragment of from 20 amino acids in length to 92 amino acids in length and having an amino acid sequence which is identical to an N-terminal amino acid sequence of SEQ ID NO: 2 of the same length as the first peptidyl fragment or having an amino acid sequence which differs by one or two residues from the N-terminal sequence of SEQ ID NO:2 of the same length;
      an arginine or lysine residue or at least one cleavable peptidyl fragment;
      a human insulin precursor peptidyl fragment comprising the human insulin A chain and the human insulin B chain;
      wherein the arginine or lysine residue or the at least one cleavable peptidyl fragment links the first peptidyl fragment and the human insulin precursor fragment; and
      wherein the first peptidyl fragment is capable of increasing the yield of the bioactive conformation of the insulin precursor formed from contacting the recombinant protein with a chaotropic auxiliary agent as compared to the yield of the bioactive conformation of the insulin precursor formed from contacting the same recombinant protein lacking the first peptidyl fragment with the chaotropic agent; and
   contacting the recombinant protein with an aqueous medium comprising the chaotropic agent,
   whereby the protein is correctly folded.

9. The method according to claim 8, wherein the aqueous medium comprises at least one chaotropic auxiliary agent.

10. The method according to claim 8, wherein the chaotropic auxiliary agent is urea.

11. The method according to claim 10, wherein the urea is present in a concentration between about 2 M and 8 M.

12. The method according to claim 11, wherein the urea is present in a concentration between about 3 M to 6 M.

13. The method according to claim 8, wherein the aqueous medium further comprises a mercaptan.

14. The method according to claim 13, wherein the mercaptan is selected from the group consisting of dithiothreitol, dithioerythrol, 2-mercaptoethanol, cysteine, methyl thioglycolate, 3-mercapto-1,2-propanediol and 3-mercaptopropionic acid.

15. The method according to claim 13, wherein the mercaptan is 2-mercaptoethanol.

16. The method according to claim 9, wherein the aqueous medium has a pH between about 8 and 10.5.

17. The method according to claim 9, wherein the aqueous medium has a pH between about 9 and 10.

18. The method according to claim 9, wherein the recombinant protein is present in the aqueous medium in a concentration between about 0.05 and 15 grams per liter.

19. The method according to claim 9, wherein the recombinant protein is present in the aqueous medium in a concentration between about 0.5 and 5 grams per liter.

20. The method according to claim 9, wherein the recombinant protein is present in the medium in a concentration between about 2 and 3 grams per liter.

21. The method according to claim 8, wherein the recombinant protein is contacted with a mercaptan.

22. The method according to claim 21, wherein the mercaptan yields less than 5—SH radical of the mercaptan per cysteine residue of recombinant protein.

23. The method according to claim 21, wherein sufficient mercaptan is provided to yield between about 0.07 to about 1.0—SH radical of the mercaptan per cysteine residue of recombinant protein.

24. The method according to claim 8, further comprising isolating a portion of the expressed recombinant protein which is in the bioactive conformation.

25. The method according to claim 24, wherein the isolating is performed by ultrafiltration.

26. The method according to claim 25, wherein the ultrafiltration is performed at a pH between about 8 and 11.

27. The method according to claim 25, wherein the ultrafiltration is performed at a pH between about 9 and 10.

28. The method according to claim 8, wherein the human insulin precursor peptidyl fragment is capable of being bound by an anti-human-insulin antibody.

29. The method according to claim 8, wherein the amino acid sequence of the human insulin precursor peptidyl fragment is the amino acid sequence of SEQ ID NO:4.

30. The method according to claim 8, wherein the amino acid sequence of the human insulin precursor peptidyl fragment is the amino acid sequence of SEQ ID NO:5.

31. The method according to claim 8, wherein the human insulin precursor peptidyl fragment consists of the A chain and B chain amino acid sequences of human insulin and therebetween a removable amino acid sequence of between 1 and 34 residues in length.

32. The method according to claim 8, wherein the amino acid sequence of the first peptidyl fragment is identical to an amino acid sequence of SEQ ID NO:1.

33. The method according to claim wherein the amino acid sequence of the first peptidyl fragment is identical to an amino acid sequence of SEQ ID NO:2.

34. The method according to claim 8, wherein the first peptidyl fragment is between 20 and 49 residues in length.

35. The method according to claim 8, wherein the at least one cleavable peptidyl fragment is an Arg or Lys residue.

36. The method according to claim 8, wherein the at least one cleavable peptidyl fragment is at least 2 amino acids in length and has a C-terminal amino acid residue selected from the group consisting of Arg and Lys.

37. The method of claim 8, wherein the human insulin A chain is identical in amino acid sequence to the amino acid sequence of residues 32–52 of SEQ ID NO:5 and the human B chain is identical in amino acid sequence to the amino acid sequence of residues 1–30 of SEQ ID NO:5.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 49 amino acids
       (B) TYPE: amino acid
       (C) STRANDEDNESS: <Unknown>
       (D) TOPOLOGY: linear (ii) MOLECULE TYPE: protein (xi) SEQUENCE DESCRIPTION: SEQ ID NO: 1:

```
Met Phe Pro Thr Ile Pro Leu Ser Arg Leu Phe Asp Asn Ala Met Le
1               5                   10                  15

Arg Ala His Arg Leu His Gln Leu Ala Phe Asp Thr Tyr Gln Glu Ph
            20                  25                  30

Glu Glu Ala Tyr Ile Pro Lys Glu Gln Lys Tyr Ser Phe Leu Gln As
        35                  40                  45

Pro
```

(2) INFORMATION FOR SEQ ID NO: 2:

(i) SEQUENCE CHARACTERISTICS:
       (A) LENGTH: 92 amino acids
       (B) TYPE: amino acid
       (C) STRANDEDNESS: <Unknown>
       (D) TOPOLOGY: linear (ii) MOLECULE TYPE: protein (xi) SEQUENCE DESCRIPTION: SEQ ID NO: 2:

```
Met Phe Pro Thr Ile Pro Leu Ser Arg Leu Phe Asp Asn Ala Met Le
1               5                   10                  15

Arg Ala His Arg Leu His Gln Leu Ala Phe Asp Thr Tyr Gln Glu Ph
            20                  25                  30

Glu Glu Ala Tyr Ile Pro Lys Glu Gln Lys Tyr Ser Phe Leu Gln As
        35                  40                  45

Pro Gln Thr Ser Leu Ser Phe Ser Glu Ser Ile Pro Thr Pro Ser As
    50                  55                  60

Arg Glu Glu Thr Gln Gln Lys Ser Asn Leu Glu Leu Leu Arg Ile Se
65                  70                  75                  80

Leu Leu Leu Ile Gln Ser Trp Leu Glu Pro Val Gln
                85                  90
```

(2) INFORMATION FOR SEQ ID NO: 3:

(i) SEQUENCE CHARACTERISTICS:
       (A) LENGTH: 6 amino acids
       (B) TYPE: amino acid
       (C) STRANDEDNESS: <Unknown>
       (D) TOPOLOGY: linear (ii) MOLECULE TYPE: protein (xi) SEQUENCE DESCRIPTION: SEQ ID NO: 3:

```
Leu Gly Thr Gly Pro Arg
1               5
```

(2) INFORMATION FOR SEQ ID NO: 4:

(i) SEQUENCE CHARACTERISTICS:
        (A) LENGTH: 86 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 4:

```
Phe Val Asn Gln His Leu Cys Gly Ser His Leu Val Glu Ala Leu Ty
1               5                   10                  15

Leu Val Cys Gly Glu Arg Gly Phe Phe Tyr Thr Pro Lys Thr Arg Ar
            20                  25                  30

Glu Ala Glu Asp Leu Gln Val Gly Gln Val Glu Leu Gly Gly Gly Pr
        35                  40                  45

Gly Ala Gly Ser Leu Gln Pro Leu Ala Leu Glu Gly Ser Leu Gln Ly
    50                  55                  60

Arg Gly Ile Val Glu Gln Cys Cys Thr Ser Ile Cys Ser Leu Tyr Gl
65              70                  75                      80

Leu Glu Asn Tyr Cys Asn
                85
```

(2) INFORMATION FOR SEQ ID NO: 5:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

```
Phe Val Asn Gln His Leu Cys Gly Ser His Leu Val Glu Ala Leu Ty
1               5                   10                  15

Leu Val Cys Gly Glu Arg Gly Phe Phe Tyr Thr Pro Lys Thr Arg Gl
            20                  25                  30

Ile Val Glu Gln Cys Cys Thr Ser Ile Cys Ser Leu Tyr Gln Leu Gl
        35                  40                  45

Asn Tyr Cys Asn
        50
```

(2) INFORMATION FOR SEQ ID NO: 6:

(i) SEQUENCE CHARACTERISTICS:
        (A) LENGTH: 107 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

```
Met Phe Pro Thr Ile Pro Leu Ser Arg Leu Phe Asp Asn Ala Met Le
1               5                   10                  15

Arg Ala His Arg Leu His Gln Leu Ala Phe Asp Thr Tyr Gln Glu Ph
            20                  25                  30

Glu Glu Ala Tyr Ile Pro Lys Glu Gln Lys Tyr Ser Phe Leu Gln As
        35                  40                  45

Pro Leu Gly Thr Gly Pro Arg Phe Val Asn Gln His Leu Cys Gly Se
    50                  55                  60
```

```
His Leu Val Glu Ala Leu Tyr Leu Val Cys Gly Glu Arg Gly Phe Ph
65                  70                  75                  80

Tyr Thr Pro Lys Thr Arg Gly Ile Val Glu Gln Cys Cys Thr Ser Il
                85                  90                  95

Cys Ser Leu Tyr Gln Leu Glu Asn Tyr Cys Asn
                100                 105
```

(2) INFORMATION FOR SEQ ID NO: 7:

(i) SEQUENCE CHARACTERISTICS:
        (A) LENGTH: 150 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

```
Met Phe Pro Thr Ile Pro Leu Ser Arg Leu Phe Asp Asn Ala Met Le
1               5                   10                  15

Arg Ala His Arg Leu His Gln Leu Ala Phe Asp Thr Tyr Gln Glu Ph
                20                  25                  30

Glu Glu Ala Tyr Ile Pro Lys Glu Gln Lys Tyr Ser Phe Leu Gln As
            35                  40                  45

Pro Gln Thr Ser Leu Ser Phe Ser Glu Ser Ile Pro Thr Pro Ser As
        50                  55                  60

Arg Glu Glu Thr Gln Gln Lys Ser Asn Leu Glu Leu Leu Arg Ile Se
65                  70                  75                  80

Leu Leu Leu Ile Gln Ser Trp Leu Glu Pro Val Gln Leu Gly Thr Gl
                85                  90                  95

Pro Arg Phe Val Asn Gln His Leu Cys Gly Ser His Leu Val Glu Al
                100                 105                 110

Leu Tyr Leu Val Cys Gly Glu Arg Gly Phe Phe Tyr Thr Pro Lys Th
            115                 120                 125

Arg Gly Ile Val Glu Gln Cys Cys Thr Ser Ile Cys Ser Leu Tyr Gl
        130                 135                 140

Leu Glu Asn Tyr Cys Asn
145                 150
```